United States Patent [19]
Milosevic et al.

[11] Patent Number: 5,177,561
[45] Date of Patent: Jan. 5, 1993

[54] PURGING OF OPTICAL SPECTROMETER ACCESSORIES

[75] Inventors: Milan Milosevic, Fishkill; Nicolas J. Harrick, Ossining, both of N.Y.

[73] Assignee: Harrick Scientific Corp., Ossining, N.Y.

[21] Appl. No.: 831,529

[22] Filed: Feb. 5, 1992

Related U.S. Application Data

[63] Continuation-in-part of Ser. No. 546,082, Jun. 29, 1990, Pat. No. 5,088,821, and a continuation-in-part of Ser. No. 762,577, Sep. 19, 1991.

[51] Int. Cl.⁵ .................... G01J 3/02; G01N 21/01
[52] U.S. Cl. .................................. 356/326; 356/244
[58] Field of Search ............. 356/300, 319, 326, 328, 356/346, 244

[56] References Cited

U.S. PATENT DOCUMENTS

| 4,322,165 | 3/1982 | Ellebracht et al. | 356/316 |
| 4,469,441 | 9/1984 | Bernier et al. | 356/316 |
| 4,640,617 | 2/1987 | Hughes et al. | 356/346 |
| 4,657,390 | 4/1987 | Doyle | 356/346 |
| 4,784,488 | 11/1988 | Doyle et al. | 356/346 |
| 4,812,041 | 3/1989 | Doyle | 356/346 |

Primary Examiner—F. L. Evans

[57] ABSTRACT

Optical spectroscopy in a purging atmosphere wherein an optical accessory is gas-tight coupled in the spectrometer sample compartment to the open beam port of the spectrometer, whereby the same purging gas used by the spectrometer can be employed to purge the accessory. Where the accessory allows external sample placement or external adjustments, rapid sample changing or adjustment is possible without breaking the purge seal. In another embodiment, the accessory has its own purge inlet and sealed windows for receiving the spectrometer beam.

8 Claims, 5 Drawing Sheets

PURGING OF OPTICAL SPECTROMETER ACCESSORIES

RELATED CASES

This application is a continuation-in-part of two earlier filed applications by U.S. Ser. Nos. 546,082 (now U.S. Pat. No. 5,088,821) and (still pending 762,577, filed respectively, on Jun. 29, 1990 and Sep. 19, 1991.

BACKGROUND OF THE INVENTION

This invention relates to optical spectroscopy, and in particular to the purging of attachments or accessories designed for use with optical spectrometers.

By purging is meant the introduction and flushing with a suitable atmosphere of the optical path sections of a spectrometer or its attachment for the purpose of minimizing or eliminating the ambient atmosphere that would otherwise be present. This is done to remove extraneous spectral artifacts from sample spectra and to enhance energy throughout. Purge atmosphere is meant to include any gas or any combination of gases which have satisfactory optical properties in the wavelength range of interest. Although purging is especially useful for single beam instruments in the mid-infrared region of the spectrum, where sample and background spectra are taken independently and where ambient atmospheric carbon dioxide and water interfere, this invention is meant to apply to the purging of attachments used in all optical spectrometers, regardless of spectrometer design or wavelength range. Suitable atmospheres are nitrogen, argon, helium, or hydrogen gas. The purge atmosphere is typically supplied at a pressure slightly above ambient pressure, so that it tends to displace the ambient air in the region of interest. Seals are generally provided to seal off the purged region from the ambient atmosphere but the seals are relatively primitive since any leakage which will occur at the seals is from the higher pressure purged region to the ambient, and thus causes little harm.

Conventional commercially available spectrometers generally provide a purge facility in several different ways. An enclosure can be provided over the sample compartment into which open entrance and exit beam ports for the optical beam. These ports are also used to supply purge gas to the sample compartment. When the spectrometer interior is purged, so will the enclosed sampling compartment be purged.

An alternative is to provide a transparent window that seals off a port in the spectrometer wall, through which the beam can enter and exit for use with external accessories, in which case a purge port can be provided in the spectrometer wall to which a tube can be connected at one end. The opposite tube end would be connected to the accessory which would mimic the sample compartment of the spectrometer.

The problem most often encountered with the conventional system is the time delay as a result of, for example, changing samples within the attachment located within the enclosed sample compartment. This requires breaking the seal to access the sample thus allowing ambient atmosphere into the system. It typically takes 20 minutes to re-purge the instrument. Hence, 20 minutes are wasted each time a new sample is to be analyzed.

With the external accessory in the conventional design, again the system seal is broken when sample changes or other adjustments become necessary, resulting in the same unavoidable delay while the system is re-purging.

SUMMARY OF THE INVENTION

The main object of the invention is an attachment or accessory construction that avoids the need to re-purge the system when sample changing or other adjustments are needed, or which greatly reduces the re-purging time.

In accordance with one aspect of the invention, the attachment or accessory is enclosed in a substantially sealed or gas tight enclosure provided with a port through which a optical beam as well as a purge atmosphere can flow. The accessory is designed to seat in the spectrometer's sample compartment. Means are provided to couple in a substantially sealed manner the accessory port to the entrance or exit port of the spectrometer. When the spectrometer is purged, so will the accessory be similarly purged. Preferably the accessory is designed such that the sample can be placed on an external wall of the accessory enclosure. Hence, sample changing will not require breaking the seal.

In accordance with another aspect of the invention, the accessory is enclosed and provided with a port that can be connected to a supply of purge gas. In this case, the spectrometer and accessory would be separately purged. If sample changing becomes necessary where the sample is inside the enclosure, the spectrometer seal need not be broken; only the accessory seal. Thus, the volume to re-purge is minimized, reducing the re-purging time. Preferably, by providing for external sample placement, or adjustments from the outside of the accessory enclosure, even the accessory seal need not be broken.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

DETAILED DESCRIPTION OF THE PREFERRED EMBODIMENTS

As used herein, "dependent purging" means purging of sample compartment attachments or accessories that have relatively small volumes and where the open (non-windowed) optical beam entrance and exit beam ports of the spectrometer give direct access to the purge reservoir of the optical bench of the spectrometer and to which the accessory is directly linked.

"Independent purging" means purging of attachments or accessories designed for external use outside the spectrometer where connections to the purge reservoirs of the spectrometer are impractical. Independent purging is more efficient than other techniques as only the relatively small volume in the optical path (which must be purged) can be purged. This efficiency is especially useful for sample compartment attachments where the alternative is to purge the entire relatively large sample compartment, a lengthy process which is repeated each time the sample compartment cover is opened to introduce a new sample. With independent purging, rapid sample exchange is possible as the sample compartment can remain open with the purge atmosphere still intact.

Independent and dependent purging in accordance with the invention is useful for sample compartment attachments that are intended for use in spectrometers that may have either windowed or open optical beam entrance and exit beam ports. It can be used with accessories or attachments designed for use in the following disciplines: transmission spectroscopy of solids, liquids, and gases; external (specular) reflection spectroscopy; internal reflection (attenuated total reflection) spectroscopy; diffuse reflection spectroscopy; emission spectroscopy. It is especially valuable in connection with accessories designed for internal reflection, and for external and diffuse reflection spectroscopy, because in those applications the accessory can be configured to receive the sample on the outside of the enclosure so that the purge seal need not be broken to change samples.

Figure 1:
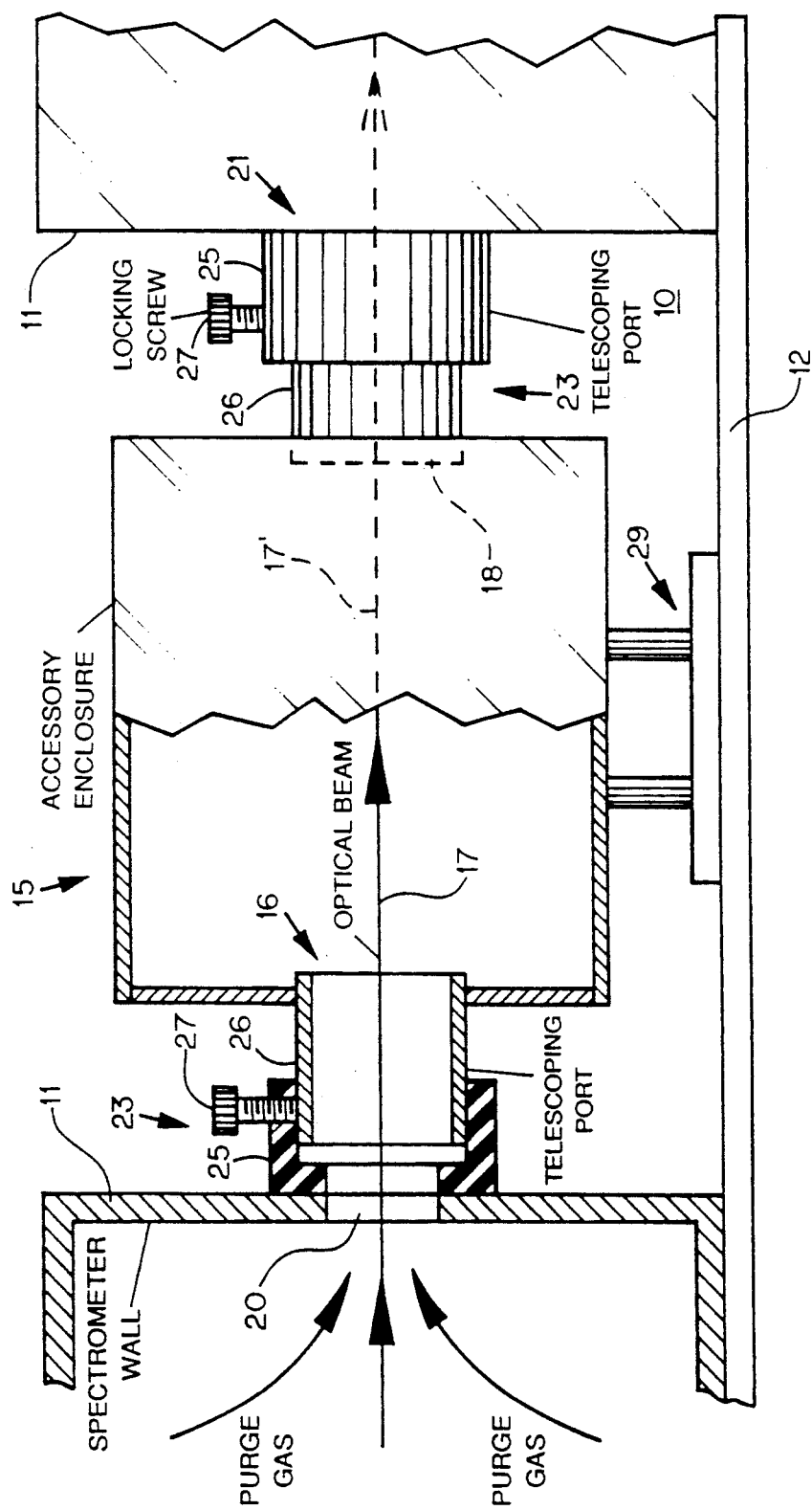
FIG. 1 is a schematic, partly cross-sectional, partly elevational view of one form of implementation of the invention, with the accessory optics omitted.

FIG. 1 is a schematic, partly cross-sectional, partly elevational view of one form of purge equipment in accordance with the invention in an implementation of dependent purging. FIG. 1 shows the sample compartment 10 of a typical optical spectrometer. The sample compartment 10 is bounded at the sides by spectrometer walls 11 and at the bottom by a base or support 12. The top of the sample compartment 10 is open to ambient atmosphere.

Seated on the base 12 is an accessory 15, which is completely enclosed in a substantially gas-tight manner. The internal optics is not shown, but the accessory is designed to receive at an entrance port 16 an optical beam 17 from the spectrometer, cause the beam to interact with a sample (not shown), and then redirect the modulated optical beam 17' via an exit port 18 in the opposite enclosure wall back into the spectrometer for the usual processing. The spectrometer in this case has open exit 20 and entrance ports 21 for the optical beam.

The spectrometer interior is sealed and conventionally provided with a purge facility for purging its interior. The supplied purge gas would thus flow as shown into the sample compartment via the open ports 20 and 21.

In accordance with the invention, means are provided for coupling the accessory entrance port 16 to the spectrometer exit port 20, and the accessory exit port 18 to the spectrometer entrance port 21 in a substantially sealed manner, so that the purge gas will also purge the accessory enclosure 15. In a preferred embodiment, telescoping adaptors 23 are provided for coupling the spectrometer ports 20, 21 to the accessory ports 16, 18. The adaptors 23, as shown, may simply comprise two telescoping cylinders 25, 26 held together by a locking screw 27. The part 26 connected to the accessory can be of metal or other materials. Preferably, the part 25 is made of rubber or a similar soft material so it can press against and seal to the spectrometer walls 11. As mentioned, a good seal is not imperative due to the higher purge pressure.

In the FIG. 1 embodiment, the spectrometer ports are open and supply both the optical beam as well as the purge gas. The accessory sits on a stand 29 in the sample compartment 10. The stand height is adapted so that the accessory and spectrometer ports line up.

The accessory can be of the variable angle reflection type described in our U.S. Pat. No. 5,048,971, issued Sep. 17, 1991, whose contents are herein incorporated by reference, in which case the optics would be enclosed and the adaptors 23 provided for connection to the spectrometer ports. While in this accessory the sample is in the interior, a frequent use is for making a number of measurements on the same sample but at different angles of incidence. It is relatively simple to modify the accessory if necessary so that the control for changing the angle of incidence on the sample is external to the enclosure, with the result that the different measurements can be made with that accessory seated in the sample compartment hooked up to the spectrometer ports without breaking the purge seal.

Figure 1A:
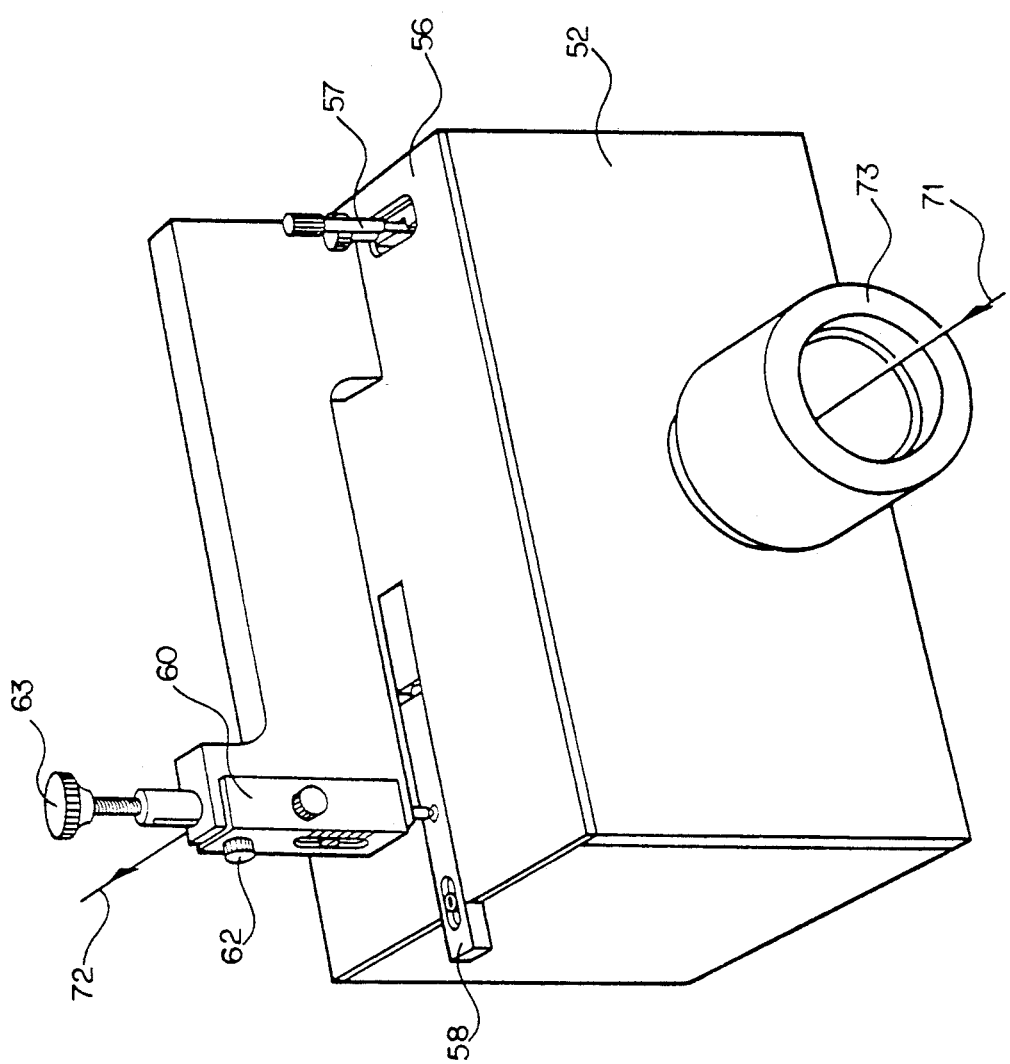
FIG. 1A shows a modification of an accessory embodying the invention.

Another example of an accessory useful in the implementation illustrated in FIG. 1 is the reflection accessory described in the said copending application, Ser. No. 762,577, whose contents are herein incorporated by reference. This is illustrated in FIG. 1A, with the gas-tight enclosure designated 52 with a lid 56 through which protrudes hand adjustments 57 for adjusting the accessory's optical elements mounted inside the enclosure 52. The sample is mounted on top of member 58, and the cantilevered member 60 is used to apply pressure to the sample via knobs 62 and 63. The incoming beam is referenced 71 and is received via a sealed port, and the exiting beam is referenced 72. Again, it is a relatively simple matter to provide the enclosure with adaptors 73 for connection to the spectrometer open ports. In the case of this accessory, the sample is external to the enclosure of the accessory, and thus can be readily changed without breaking the purge seal. This accessory, like the variable angle patented accessory, can also be provided with its own purge port for connection to a tubing supplying a suitable purge gas, and thus can be operated outside of the sample compartment. In this case, optics would be needed to direct the spectrometer beam into the accessory, and the modulated beam back to the spectrometer for processing. This will be straightforward. Also, in this case, the accessory port would be sealed. This then is an example of independent purging.

Figure 2A:
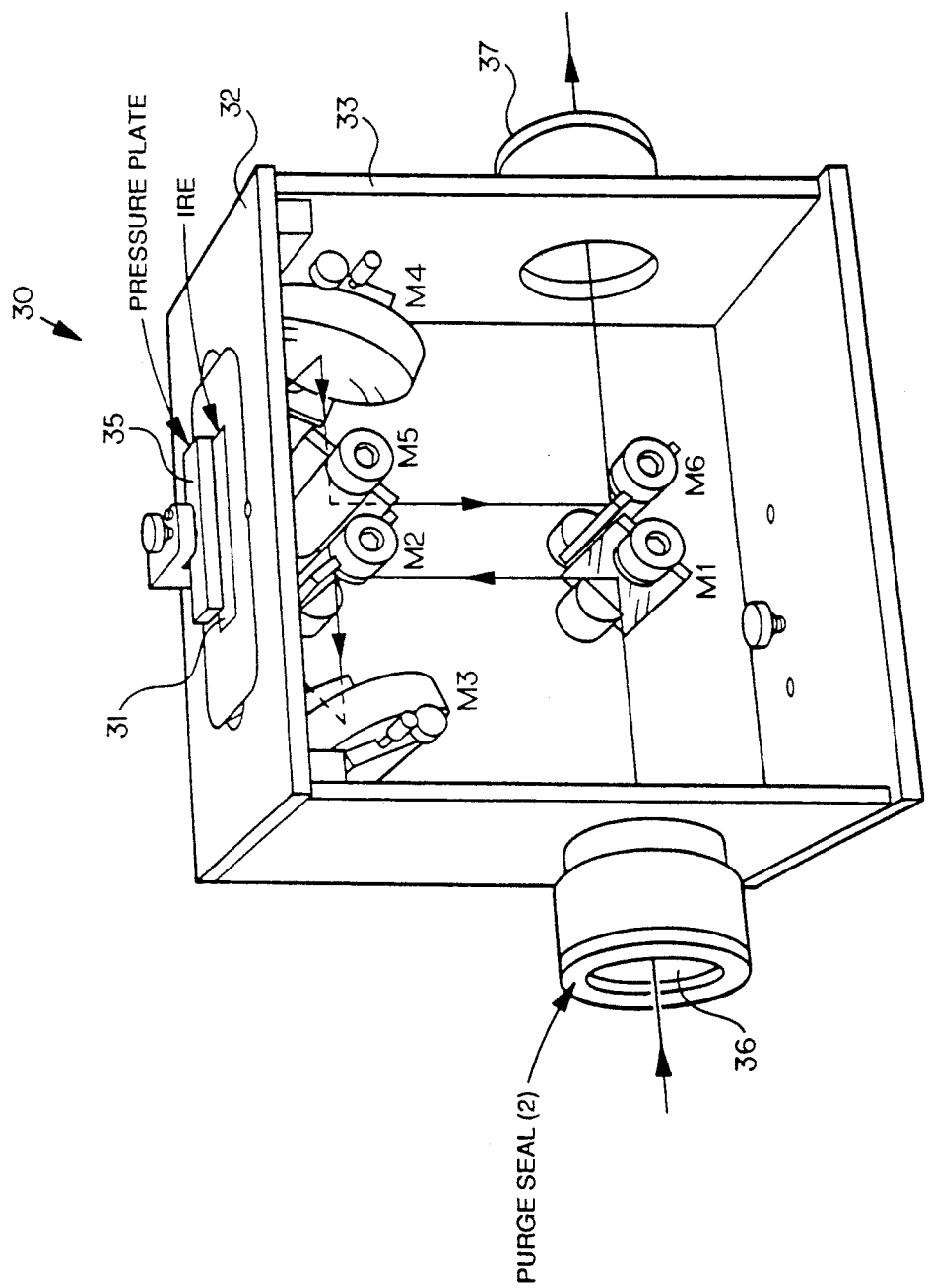
FIG. 2 shows a typical accessory of the invention, with FIG. 2a showing the interior via one wall from which the cover was removed, and FIG. 2b showing the fully assembled accessory with the cover replaced.
Figure 2B:
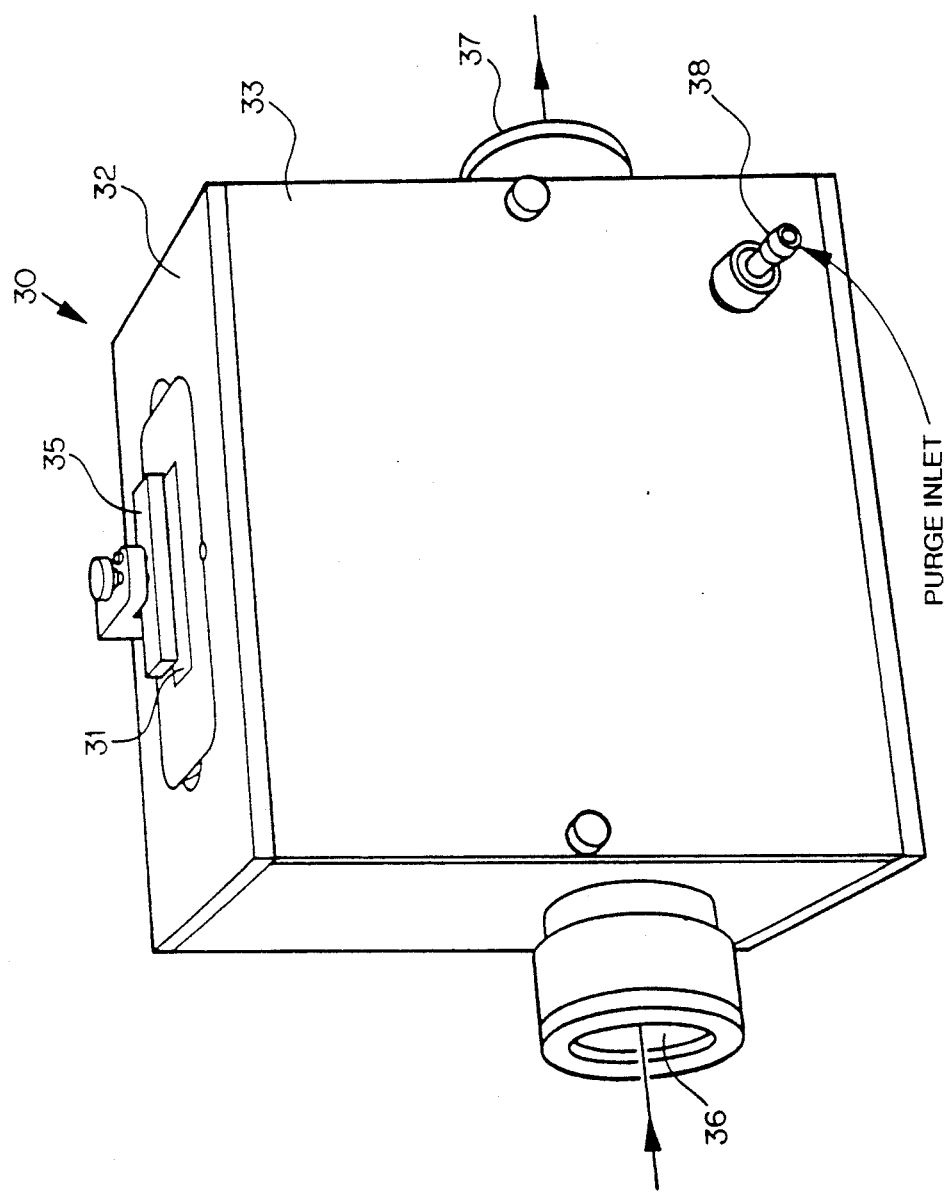

Another example of an accessory suitable for use with dependent or independent purging is illustrated in FIGS. 2(a) and 2(b). In this case, the accessory 30 is designed for internal reflection spectroscopy using an IRE 31 mounted in the top wall 32 of a sealed enclosure 33. The sample (not shown) is placed on top of the IRE, and pressure applied via a pressure plate 35. The beam enters via a sealed window 36 and is conveyed by suitable optics M1, M2 and M3 to enter the IRE at its lower side. It propagates in the well known manner down the IRE, interacting with the sample, exits at the IRE opposite end, and is then directed by optics M4, M5, and M6 out a sealed exit window 37. This accessory 30 can sit in an open sample compartment in the manner shown in FIG. 1, and be separately, independently purged via a purge inlet fitting 38. Alternatively, the windows 36, 37 can be opened, and the enclosure coupled to the spectrometer ports by means of the adaptor 23 in a dependent purging mode.

Our copending application Ser. No. 546,082, now U.S. Pat. No. 5,088,821 whose contents are herein incorporated by reference, describe a number of remote sampling terminals connected by way of light pipes to a spectrometer. In this case, the sampling terminals are enclosed and purged by way of the light pipe or can be separately purged, or both. In several instances, such sampling terminals employ an enclosure wall against which a sample can be positioned for analysis by one of several different reflection or emission techniques. Such an accessory lends itself well to use of the invention in its independent mode, since the sampling terminals are typically located at some distance from the spectrometer.

It is clear from the examples given above that the invention can be applied to many different kinds of accessories and attachments for optical spectrometers, but is especially valuable in an accessory in a purgeable box with an external sample-receiving surface permitting rapid sample exchange without interrupting the purge of the spectrometer or accessory.

Figure 3:
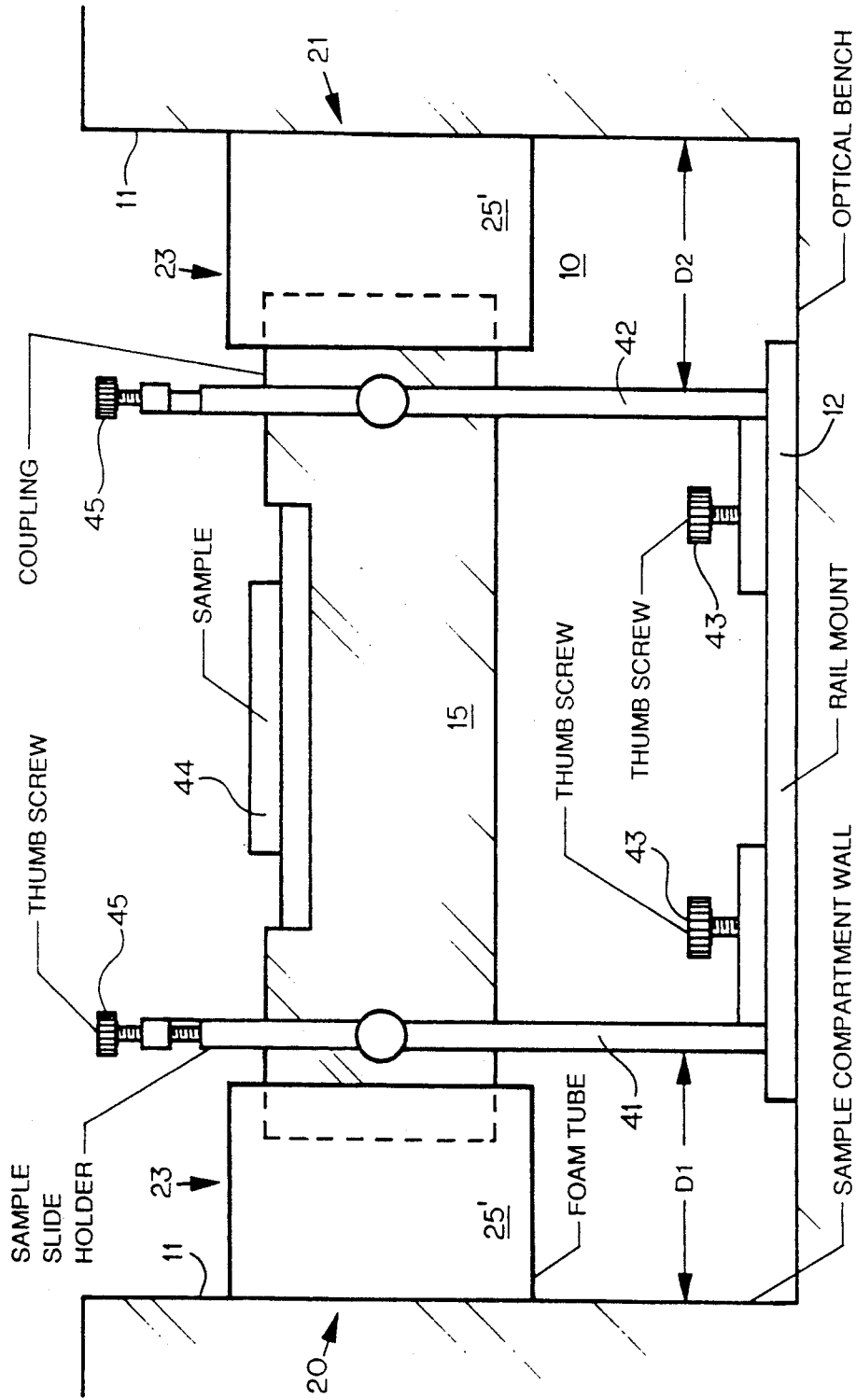
FIG. 3 is a view similar to FIG. 1 of a modification of the invention.

FIG. 3, which is similar to FIG. 1, illustrates a way of aligning the accessory 15 with the spectrometer ports 20, 21. In this case, the accessory could be mounted on vertical supports 41, 42, for example, a sample slide holder, so that the vertical height as well as the lateral position of the accessory in the sample compartment can be adjusted. The thumb screws 43 are used to lock the position of the supports 41, 42 when the distances D1 and D2 are equal. FIG. 3 also shows a foam tube 25' as part of the adaptors or couplings 23. In this case, an accessory of the type shown in FIG. 2 is illustrated, with the sample 44 on top of the accessory 15. The thumb screws 45 are used to lock the vertical position of the accessory.

It will also be appreciated that the volume of purge gas supplied to the accessory can be adjusted or controlled by, for example, inserting a valve at the purge inlet 38 of the FIG. 2 accessory.

While the spectrometers have been shown with separate beam exit and entrance ports to the sample compartment, the invention can be employed with a spectrometer having a single port for receiving an optical beam, such as in emission spectroscopy, or having a single port used jointly for an exiting and entering beam.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. The combination of:
   (a) an optical spectrometer having a fixed sampling compartment bounded by walls containing at least one port for an optical beam, said port being open whereby a purging gas supplied within the spectrometer can exit the port to the sampling compartment, said sampling compartment being open,
   (b) an independent changeable optical accessory configured to fit within the sampling compartments of plural spectrometers and having means for receiving a sample to be analyzed by means of the spectrometer optical beam and an entrance port for the optical beam, said accessory being enclosed and being configured to seat within the open sampling compartment,
   (c) means for coupling in a substantially gas-tight manner the accessory entrance port to the spectrometer exit port whereby the accessory can be purged while seated in the open sampling compartment by the same purging gas used for the spectrometer.

2. The combination of claim 1, wherein the coupling means comprises a telescoping tube.

3. The combination of claim 1, wherein the coupling means comprises a soft material.

4. The combination of claim 1, wherein the coupling means comprises a foam tube.

5. The combination of claim 1, further comprising means for positioning the accessory relative to the spectrometer port.

6. The combination of claim 1, wherein the accessory is constructed for external or internal reflection spectroscopy.

7. An optical accessory for use in reflection optical spectroscopy with a standard spectrometer, comprising:
   a gas-tight enclosure for optics,
   a port for receiving an optical beam, said port being sealed off,
   an inlet for a purge gas,
   means on the outside of the enclosure for manipulating the optics inside the enclosure without having to break the gas-tightness of the enclosure.

8. An optical accessory for optical spectroscopy as claimed in claim 7, wherein the accessory enclosure has an external wall and has a sample receiving surface located on the outside of the enclosure external wall for receiving and interacting with the optical beam from within the enclosure whereby samples can be exchanged without having to break the gas-tightness of the enclosure.

* * * * *